(12) United States Patent
Dukhin et al.

(10) Patent No.: US 6,915,214 B2
(45) Date of Patent: Jul. 5, 2005

(54) METHOD FOR DETERMINING ELECTRIC PROPERTIES OF PARTICLES IN LIQUIDS BY MEANS OF COMBINED ELECTROACOUSTIC AND COMPLEX CONDUCTIVITY MEASUREMENT

(75) Inventors: Andrei S. Dukhin, Goldens Bridge, NY (US); Philip J. Goetz, Essex, NY (US)

(73) Assignee: Dispersion Technology, Inc., Bedford Hills, NY (US)

( * ) Notice: Subject to any disclaimer, the term of this patent is extended or adjusted under 35 U.S.C. 154(b) by 0 days.

(21) Appl. No.: 10/440,528

(22) Filed: May 19, 2003

(65) Prior Publication Data

US 2004/0236521 A1 Nov. 25, 2004

(51) Int. Cl.[7] .............................................. G01N 31/00
(52) U.S. Cl. ...................................... 702/29; 73/865.5
(58) Field of Search ............................... 702/29, 30, 39, 702/42, 47, 48, 50, 54, 56, 57, 103, 138; 324/452, 457; 73/584, 865.5; 700/281

(56) References Cited

U.S. PATENT DOCUMENTS

| | | | | |
|---|---|---|---|---|
| 4,497,208 A | * | 2/1985 | Oja et al. ...................... | 73/584 |
| 5,059,909 A | * | 10/1991 | O'Brien ...................... | 324/457 |
| 5,245,290 A | * | 9/1993 | Cannon et al. .............. | 324/457 |
| 5,280,250 A | * | 1/1994 | Jayaweera et al. .......... | 324/452 |
| 5,293,773 A | | 3/1994 | Babchin | |
| 5,616,872 A | * | 4/1997 | O'Brien ...................... | 73/865.5 |
| 6,109,098 A | | 8/2000 | Dukhin et al. | |
| 6,535,796 B1 | * | 3/2003 | Sierro et al. ................. | 700/281 |

OTHER PUBLICATIONS

A.S. Dukhin and P.J. Goetx "Ultra Sound forCharacterizing Colloids Particle Sizing, Zeta Potential, Rheology".
R.W. O'Brien, B.R. Midmore, A.Lamb, R.J. Hunter "Electr–oacoustic Studies of Moderatly Concentrated Colloidal Suspensions" Faraday Discuss, Chem. Soc. 90,1990.
D.W. Cannon "New Developments in Electroacoustic Methods and Instrumentation", NIST 1993.
E.E. Ysaaks, N. Huang, A.J. Babchin and R.S. Chow Electroacoustic Method for monitoring the coalescence of water in oil emulsions. Collids and Surfaces, 46, 177–192 (1990).
R. Hunter "Recent Developments in the Electroacoustic Characterization of Colloidal Suspensions" Colloids and Surfaces, 141, 37–65 (1998).
S.S.Dukhin and V.N. Shilov "Dielectric Phenomena and the Double Layer in Dispersed Systems and Polyelectrolytes", J. Wiles NY 1974.

* cited by examiner

*Primary Examiner*—Marc S. Hoff
*Assistant Examiner*—Mohamed Charioui

(57) ABSTRACT

A method is described which applies the combination of Electroacoustic and Complex Conductivity measurements to characterize particle electric surface properties, such as ζ-potential, and bulk properties, such as the dielectric permittivity, in systems where conductivity data is required for applying an appropriate theoretical model for calculating output parameters from the measured data. In particular, this is important in low conducting systems for which the double layer thickness exceeds the particle radius or in the systems where particles have either high bulk dielectric permittivity or high conductivity.

5 Claims, 10 Drawing Sheets

Dielectric permittivity and conductivity of dispersion with 10%vl non-conducting particles in water with 0.1 S/m conductivity at 3 MHz. Calculated according to the Maxwell-Wagner theory.

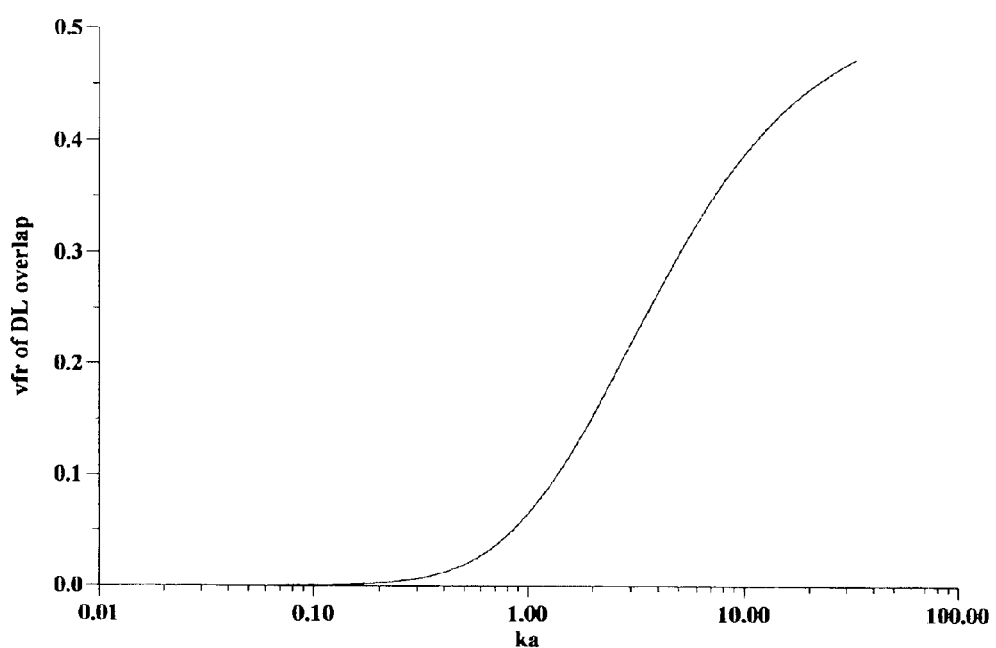
Figure 1. Estimate of the volume fraction of the overlap of the electric double layer Figure 2. Electrophoretic dynamic mobility at 3 MHz of non-conducting particles in water at 10% weight, temperature 22 °C, ζ-potential is 25 mV. Particles density is 2.2 g/cm$^3$, dielectric permittivity 3.75. Density of water is 0.997 g/cm$^3$, dielectric permittivity 79.9, dynamic viscosity 0.94 cp.
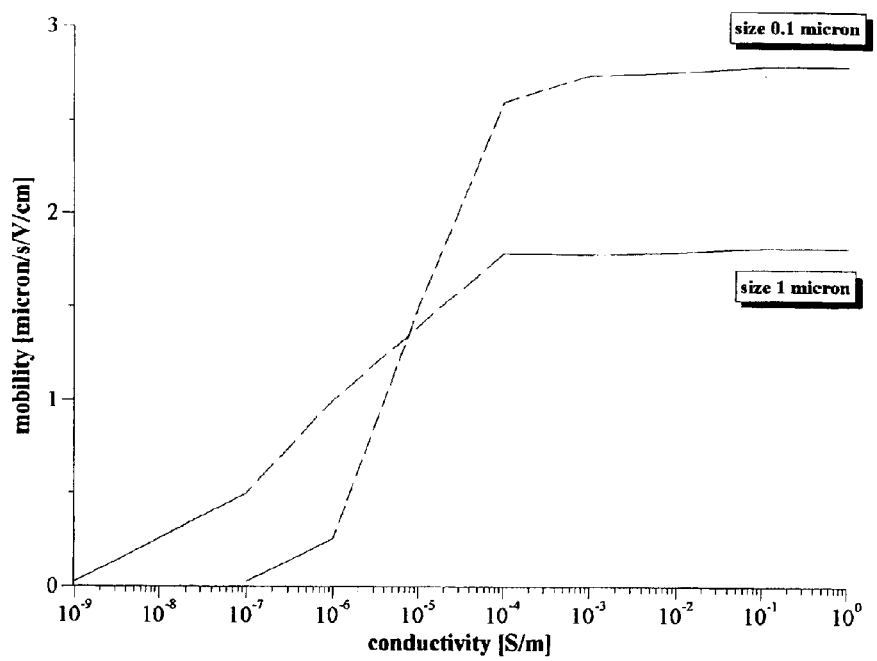

Figure 3. Electrophoretic dynamic mobility at 3 MHz of the barium titanate particles in water at 10% weight, temperature 22 C⁰, ζ-potential is 25 mV. Particles density is 5 g/cm³, dielectric permittivity 1000. Density of water is 0.997 g/cm³, dielectric permittivity is 79.9, dynamic viscosity is 0.94 cp
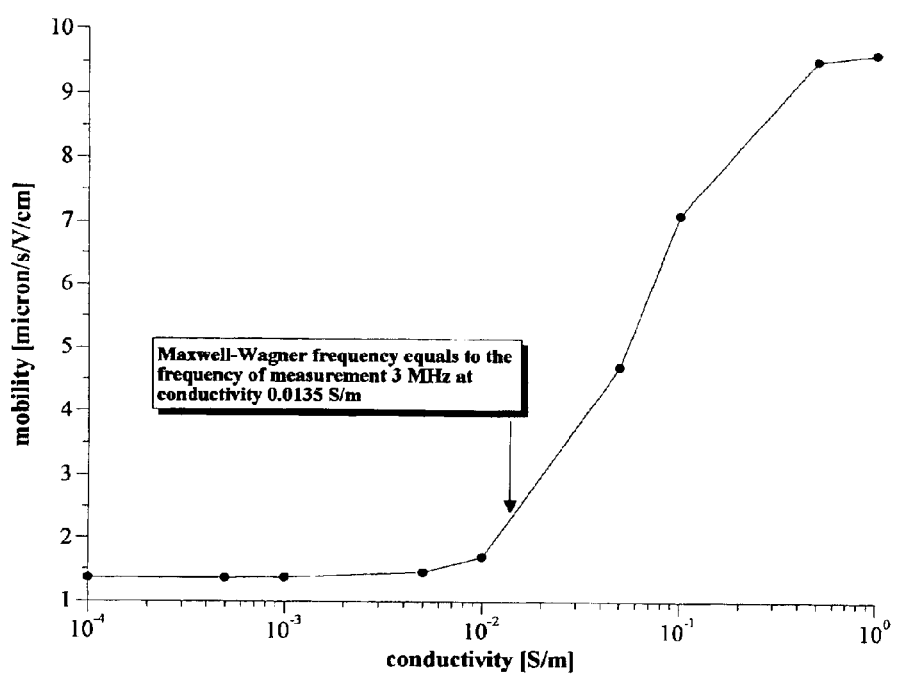

Figure 4. Dielectric permittivity and conductivity of dispersion with 10%vl non-conducting particles in water with 0.1 S/m conductivity at 3 MHz. Calculated according to the Maxwell-Wagner theory.
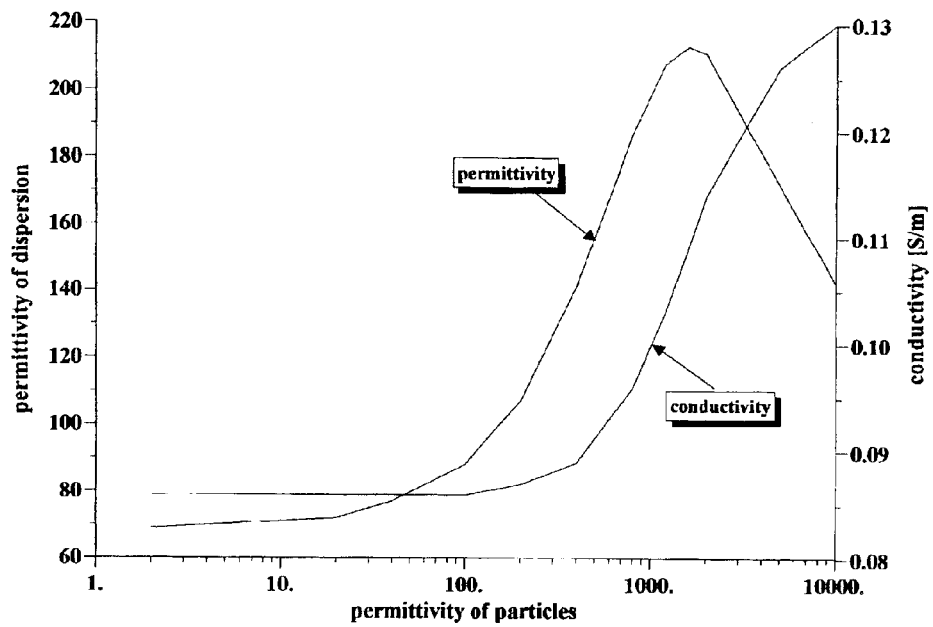

Figure 5. Verification of Maxwell-Wagner theory with aluminum hydroxide particles in water. Particle diameter is 1 micron. Two ways equilibrium dilution with supernate: from high concentration (76%wt) to lower by adding supernate to the initially concentrated dispersion, and from low concentration to higher by adding concentrated dispersion to the supernate.. Conductivity is measured at 3 MHz.

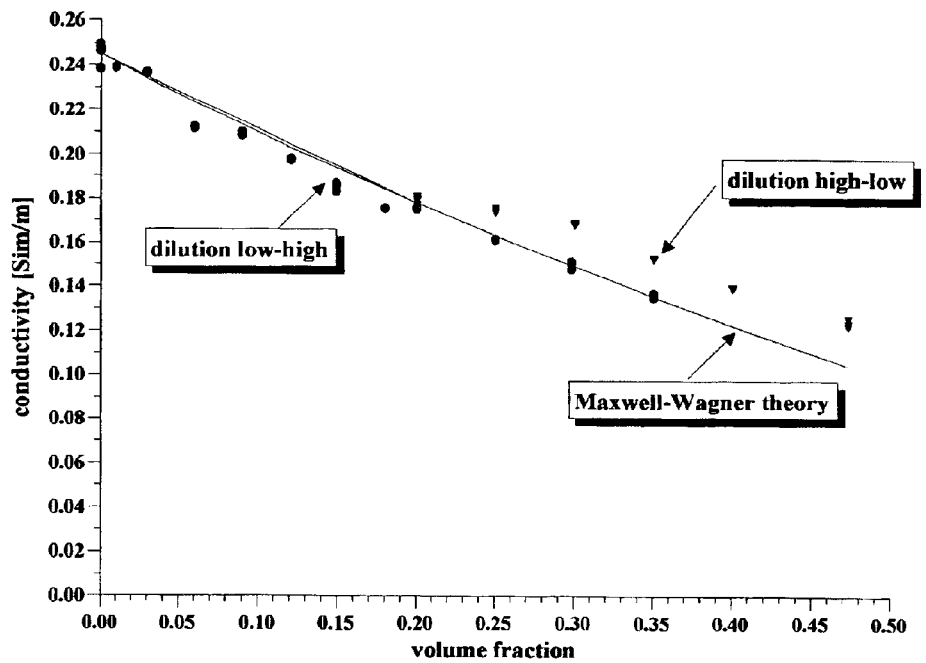

Figure 6. Colloid Vibration Current measured for iron oxide particle 15 nanometer in size in toluene-bitumen mixture with surfactant presence for various weight fractions of particles.
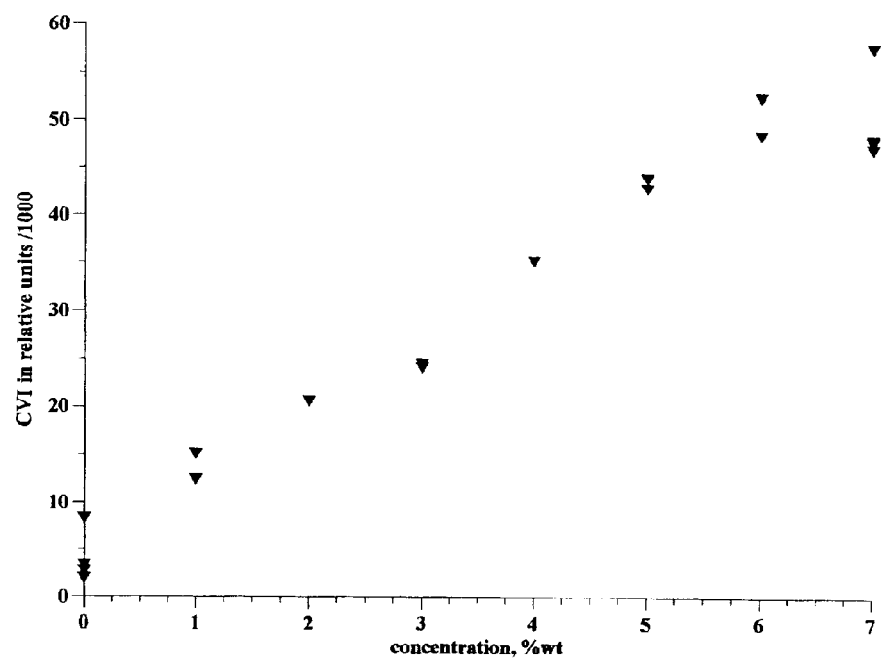

Figure 7. ζ-potential of iron oxide particle 15 nanometer in size in toluene-bitumen mixture with surfactant presence for various weight fractions of particles. These values are calculated using Electroacoustic theory with thick overlapped DLs from CVI data presented on Figure 6
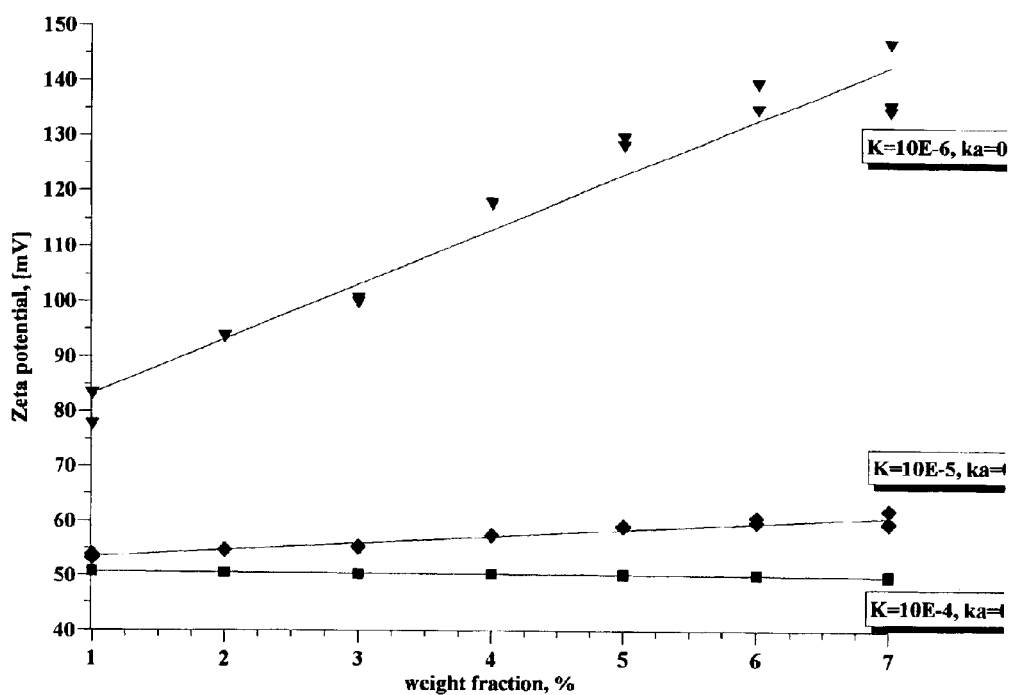

Figure 8. Imaginary part of the complex conductivity of 20%wt barium titanate in distilled measured at 3 MHz continuously with mixing and with no mixing. Value when mixing is off corresponds to the pure liquid due to the particles fast sedimentation.
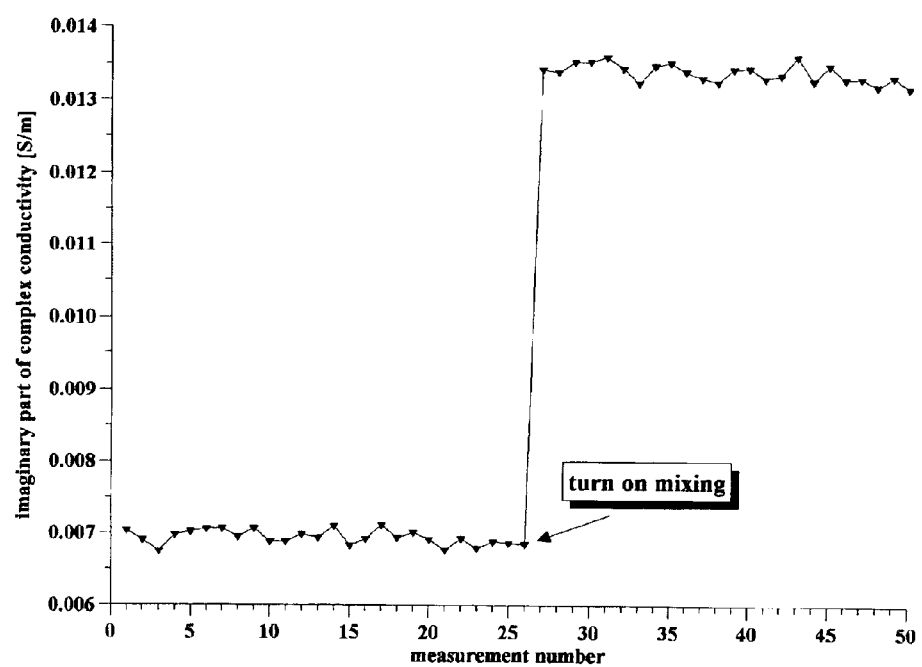

Figure 9. Titration of 20%wt barium titanate slurry. Electroacoustic and conductivity measurements are made with DT-1200 by Dispersion Technology Inc. Dielectric permittivity of particles for calculating ζ-potential is assumed as 850.
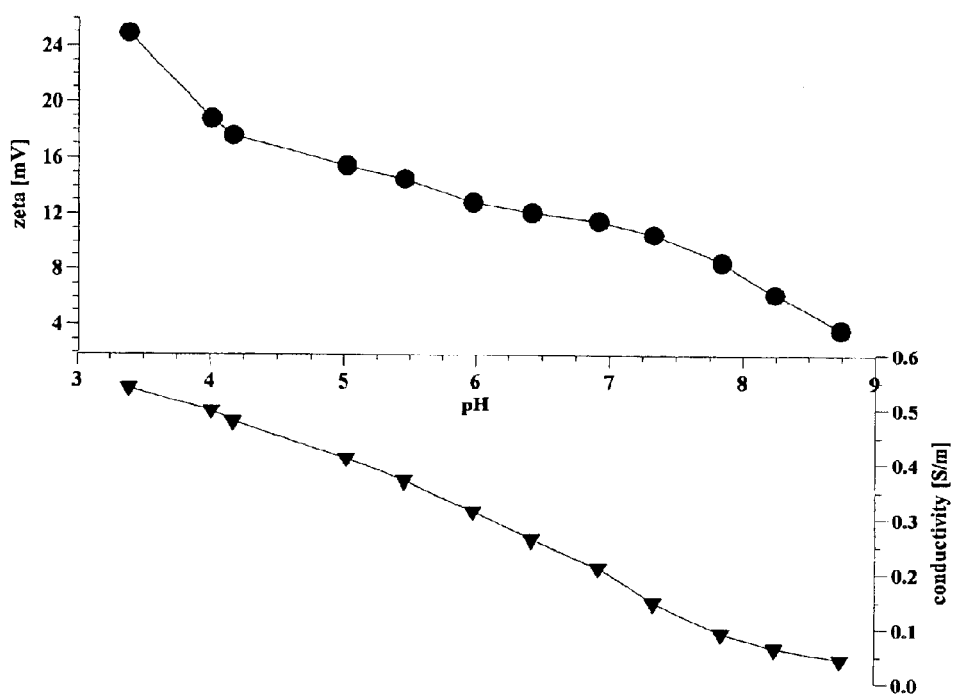

Figure 10. Titration of 20%wt barium titanate slurry. Measurement of Colloid Vibration Current phase is made with DT-1200 by Dispersion Technology Inc. Dielectric permittivity of particles for calculating theoretical phase is assumed as 850 and 3.
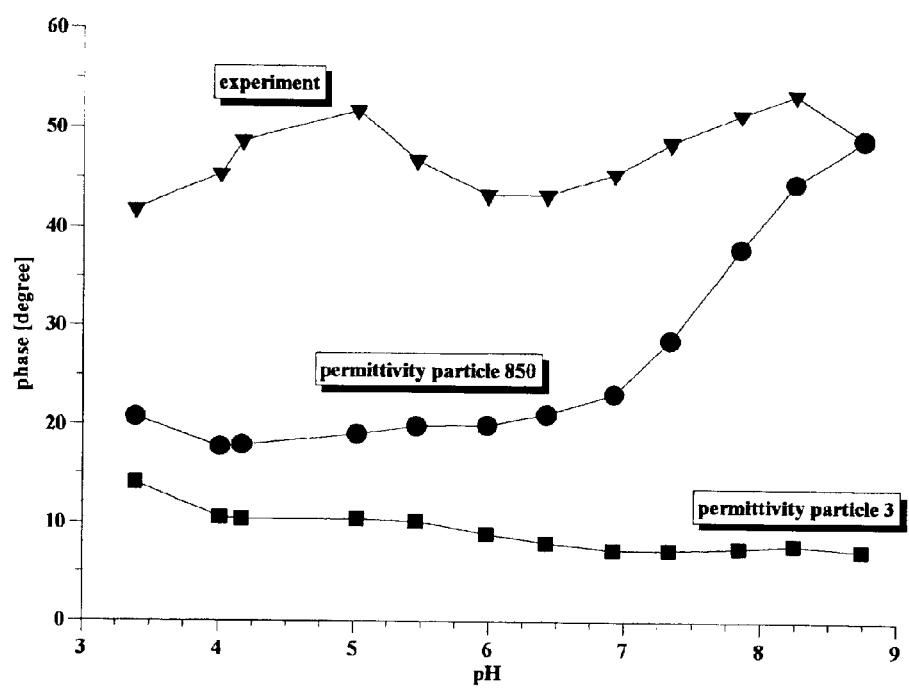

METHOD FOR DETERMINING ELECTRIC PROPERTIES OF PARTICLES IN LIQUIDS BY MEANS OF COMBINED ELECTROACOUSTIC AND COMPLEX CONDUCTIVITY MEASUREMENT

FIELD OF THE INVENTION

This invention describes a method to determine the ζ-potential of colloid particles in low-conducting liquids, or in aqueous systems when particles have either large or unknown dielectric permittivity, using not only the measured electroacoustic signal, but importantly also the measured complex conductivity.

BACKGROUND OF THE INVENTION

This invention deals with a particular kind of dispersed system (or colloid) that can be described as a collection of small particles immersed in a liquid. These particles can be either solid (dispersions), or liquid (emulsions). Such dispersed systems play an important role in the formulation of a variety of materials such as ceramics, paints, lattices, food products, paper coatings, polymer solutions, etc.

These systems all share a common feature. Because of the small particle size, the total surface area of the particles is large relative to their total volume. Therefore surface related phenomena determine their behavior in various processes. This invention applies to dispersed systems where these surface effects are dominant, corresponding to a range of particle size up to about 10 microns. The importance of these surface effects disappears for larger particles.

One of the most commonly used characteristics of these surface effects is the so-called ζ-potential. It is important because of the relationship between this parameter and the aggregation stability of many dispersions and emulsions. There are several methods with which to characterize this parameter. In dilute systems, microelectrophoresis is the most common tool. In the case of flat surfaces and very large particles, a streaming current method is useful.

This patent deals with concentrated dispersions and emulsions. The only available method with which to characterize ζ-potential in these systems, without dilution, is based on Electroacoustic phenomena. A historical overview of this effect is presented in the recently published book by Dukhin, A. S. and Goetz, P. J. "Ultrasound for characterizing colloids. Particle sizing, Zeta Potential, Rheology", Elsevier, 2002.

There are several patents that introduce methods and devices based on Electroacoustics. All of them present Electroacoustics as an independent technique that allows us to characterize ζ-potential without additional measurements, and in particular without conductivity measurement.

For instance, in U.S. Pat. No. 5,059,909 R. W. O'Brien commented on (page 10, line 60) the "Determination of particle size and electric charge" and claimed that " . . . Thus by measuring the pressure difference and short-circuit current it is possible to determine (zeta potential) without the need for conductivity measurement."

In the two other US patents by R. W. O'Brien, U.S. Pat. No. 5,616,872 "Particle size and charge measurement in multi-component colloids" and D. W. Cannon, R. W. O'Brien, U.S. Pat. No. 5,245,290 "Device for determining the size and charge of colloidal particles by measuring electroacoustic effect" there is no discussion whatsoever about the need for conductivity data.

The two earlier US patents by T. Oja, G. L. Peterson and D. W. Cannon U.S. Pat. No. 4,497,208 "Measurement of electro-kinetic properties of a solution" and by A. J. Babchin et al U.S. Pat. No. 5,293,773, "Method for determining the wetting presence of particulate solids in a multiphase liquid system", also ignore conductivity measurements.

There are claims in several publications that the absence of any need for conductivity data in extracting the ζ-potential from the measured Electroacoustic signal is an important advantage of a particular Electroacoustic method. For example, R. W. O'Brien, B. R. Midmore, A. Lamb and R. J. Hunter wrote in "Electroacoustic studies of moderately concentrated colloidal suspensions", Faraday Discuss.-Chem. Soc., 90, 1–11 (1990): " . . . From Eq.5 (ESA∝CVP*K*) it can be seen that the ESA is independent of the complex conductivity of the suspension, so the ESA is more convenient than CVP for determining the mobility. The main motivation for determining the mobility is, of course, to obtain information about the particles . . . ". Another example is review by R. J Hunter "Recent developments in the electroacoustic characterization of colloidal suspensions and emulsions", Colloids and Surfaces, A, 141, p.37–65, (1998), which make statement on the page 40 that " . . . measurement of ESA effect gives $\mu_d$ immediately, whereas one needs not only CVP, but also the complex conductivity to obtain $\mu_d$ by the alternate route . . . ".

There is a reference to the earlier work by R. W. O'Brien given by D. W. Cannon, who contributed to the "New developments in electroacoustic methods and instrumentation" NIST, 1993: " . . . O'Brien {J. Fluid Mech. 1988} has pointed out that the electrical response at the electrodes can also be measured as the short circuit current which has the advantage that the current is directly proportional to the charge of the particles while the CVP is proportional to the charge divided by the electric conductivity of the suspension".

A few years earlier the same statement had been made by E. E. Isaacs, H. Huang, A. J. Babchin and R. S. Chow, in "Electroacoustic method for monitoring the coalescence of water-in-oil emulsions", Colloids and Surfaces, 46, (1990), p. 181:" As shown by O'Brien, the measured pressure will not depend on the complex conductivity of the colloidal system, and therefore this mode of measurement can be recommended when working with colloids where the water phase is continuous. When working with oil continuous colloids, however, CVP mode of operation is preferred. The low value of the complex conductivity will provide for a significant $\Delta\Psi$ even for small values of dynamic mobility. We may say that the small conductivity of the non-polar media acts as a natural amplifier in electrokinetic measurements by ultrasound vibration potential.

$$\Delta\Psi = \frac{\varphi \Delta \rho c V_0}{K^*} \mu_d(\omega) \quad (1)$$

where $\Delta\Psi$ is potential difference between electrodes, $\phi$ is volume fraction, $\Delta\rho$ is density contrast between particle and media, $K^*$ is complex conductivity, $\mu_d$ is dynamic electrophoretic mobility."

We should make note that in our previous US patent that covers the electroacoustic method employed in the Dispersion Technology instruments (U.S. Pat. No. 6,109,098 by Dukhin, A. S. and Goetz, P. J. "Method and device for characterizing particle size distribution and zeta potential in concentrated system by means of Acoustic and Electroacoustic Spectroscopy"), we also ignored the need for conductivity measurement. Even more, we considered the Colloid Vibration Current (CVI) mode superior to the Colloid Vibration Potential (CVP) mode specifically because we then believed that the CVI mode would not require conductivity data for calculating ζ-potential.

However, several recent theoretical and experimental developments have forced us to reconsider the relationship between Electroacoustic and Conductivity measurements with regard to ζ-potential characterization. We now realize that there are several situations where the calculation of ζ-potential, from any mode of Electroacoustic signal, is impossible without conductivity data.

There are three modes of Electroacoustics, depending on the driving force: Colloid Vibration Potential (CVP), Colloid Vibration Current (CVI), and ElectroSonic Amplitude (ESA). The first two use ultrasound as a driving force, whereas the third applies an electric field as the driving force.

It has been generally accepted that one could switch from one mode to another in order to avoid the need for a conductivity measurement. For instance, O'Brien suggested switching from CVP to CVI to achieve this purpose.

We have discovered recently that such "mode switching" is sometimes not productive. There are real systems where the Electroacoustic and Conductivity effects are inexorably intertwined such that both must be measured in order to calculate ζ-potential, no matter which mode of Electroacoustic measurement is employed. We will demonstrate this fact for two important categories of dispersions and emulsions:

Low conducting systems with a thick Double Layer

Dispersions containing particles with high dielectric permittivity

Unraveling this complex relationship between the electroacoustic and conductivity measurement forms the basis for our present claim of a new method of ζ-potential characterization, applicable to a wide variety of dispersions and emulsions.

BRIEF SUMMARY OF INVENTION

The applicant describes a new method of calculating the particle ζ-potential from a measured Electroacoustic signal that extends the current theory to now include systems with a relatively low conductivity such that the double layer thickness exceeds the particles radius, and also for systems having particles with a very high and perhaps unknown dielectric permittivity. This method utilizes both the Electroacoustic data as well as measurement of the Complex Conductivity, allows automatic determination of some unknown properties of particles such as the dielectric permittivity, and by applying a new theory allows the correct calculation of the ζ-potential for conditions before not possible.

BRIEF DESCRIPTION OF THE DRAWINGS

FIG. 1. Estimate of the volume fraction of the overlap of the electric double layer FIG. 2. Electrophoretic dynamic mobility at 3 MHz of non-conducting particles in water at 10% weight, for temperature of 22° C., ζ-potential 25 mV, particles density of 2.2 g/cm$^3$, dielectric permittivity of 3.75. Density of water is 0.997 g/cm$^3$, dielectric permittivity 79.9, dynamic viscosity 0.94 cp.

FIG. 3. Electrophoretic dynamic mobility at 3 MHz of barium titanate particles in water at 10% weight, temperature 22 °C., ζ-potential is 25 mV. Particles density is 5 g/cm$^3$, dielectric permittivity 1000. Density of water is 0.997 g/cm$^3$, dielectric permittivity is 79.9, dynamic viscosity is 0.94 cp.

FIG. 4. Dielectric permittivity and conductivity of dispersion with 10% vl non-conducting particles in water with 0.1 S/m conductivity at 3 MHz. Calculated according to the Maxwell-Wagner theory.

FIG. 5 Verification of Maxwell-Wagner theory with aluminum hydroxide particles in water. Particle diameter is 1 micron. Two ways equilibrium dilution with supernate: from high concentration (76% wt) to lower by adding supernate to the initially concentrated dispersion, and from low concentration to higher by adding concentrated dispersion to the supernate. Conductivity is measured at 3 MHz.

FIG. 6. Colloid Vibration Current measured for iron oxide particle 15 nanometers in size in toluene-bitumen mixture with surfactant presence for various weight fractions of particles FIG. 7. ζ-potential of iron oxide particle 15 nanometer in size in toluene-bitumen mixture with surfactant presence for various weight fractions of particles. These values are calculated using Electroacoustic theory with thick overlapped DLs from CVI data presented on FIG. 6

FIG. 8. Imaginary part of the complex conductivity of 20% wt barium titanate in distilled measured at 3 MHz continuously with mixing and with no mixing. Value when mixing is off corresponds to the pure liquid due to the particles fast sedimentation FIG. 9. Titration of 20% wt barium titanate slurry. Electroacoustic and conductivity measurements are made with DT-1200 by Dispersion Technology Inc. Dielectric permittivity of particles for calculating ζ-potential is assumed as 850

FIG. 10. Titration of 20% wt barium titanate slurry. Measurement of Colloid Vibration Current phase is made with DT-1200 by Dispersion Technology Inc. Dielectric permittivity of particles for calculating theoretical phase is assumed as 850 and 3.

DETAILED DESCRIPTION OF INVENTION

Characterization of ζ-potential includes two steps: measurement and interpretation. This invention does not relate to the measurement part. We assume that there are commercially available instruments for measuring the Electroacoustic signal in either mode and for measuring the Complex Conductivity as well. This invention targets the interpretation part, where we calculate the ζ-potential from the measured raw data.

We start by presenting the theory of the Electroacoustic effect. We will do it separately for a "thin double layer" and then a "thick double layer". The double layer thickness, $\kappa^{-1}$, with respect to the particle radius, a, is an important parameter reflecting the influence of conductivity on the electric surface properties. The double layer thickness is related to the properties of the solution according to the formula:

$$\kappa = \sqrt{\frac{e^2 \sum_i z_i^2 n_i}{\varepsilon k T}} \quad (2)$$

where: e is an electron charge; k is the Boltzman constant, T is the absolute temperature; $n_i$, and $z_i$ are the numerical concentrations far from the charged surface and the valency (including the sign of ion's charge) of i-th kind of ions, respectively; and $\epsilon_m$ is the dielectric constant of the solvent.

For relatively conducting aqueous solutions, the double layer is usually much thinner than the particle radius ($\kappa a \gg 1$), whereas in low conducting liquids we have the opposite case (i.e. $\kappa a \ll 1$). It is possible to derive a separate analytical theory for these two cases. Introduction of these two distinct areas of $\kappa a$ values depends on the variation of the DL for different volume fractions. It is clear that increase of the volume fraction eventually leads to the overlap of particles double layers. It is also clear that in the case of the thin DL this overlap occurs at the much higher volume fraction than for the case of the thick DL. We can characterize this overlap with a critical volume fraction $\phi_{over}$ at which it occurs. A simple estimate of this critical volume fraction, $\phi_{over}$, is that volume fraction for which the Debye length is equal to the shortest distance between the particles. Thus:

$$\varphi_{over} \approx \frac{0.52}{\left(1+\frac{1}{\kappa a}\right)^3} \quad (3)$$

This dependence is illustrated in FIG. 1.

It is clear that for $\kappa a > 10$ (thin DL) we can consider the DLs as isolated entities even up to volume fractions of 0.4. We can also apply a model of the flat DL to the local parts of the particle surface.

In contrast, for $\kappa a < 0.1$ (thick DL) the double layers overlap even in very dilute suspensions. In this case we can apply a model of homogeneous double layers that fills the space between particles. This model has been suggested by V. N. Shilov and presented the first time in the International Conference on Electrokinetics in Krakov in 2002, "The theory of electroacoustics in concentrated weakly-conducting suspensions", by Yu. B. Borkovskaya, V. N. Shilov and A. S. Dukhin, Abstracts of International Symposium on Electrokinetic Phenomena, Krakow, Poland, 2002, p. 35.

These simplifications in description of the DL lead to different theoretical models for the Electroacoustic phenomena. We give here the final expressions that follow from these two limiting case theories. Unfortunately there is as yet no theory for the intermediate situation, $0.1 < \kappa a < 10$. We will use a simple interpolation between the two limiting cases to describe this region.

In addition, we present a final expression for the Maxwell-Wagner theory of the complex conductivity of heterogeneous systems.

In the following two sections we will show how these theories work for real systems, and will illustrate the errors that would be experienced if the effect of the Complex Conductivity measurement is ignored Electroacoustic Theory for Thin DL ($\kappa a > 10$).

The most recent theory of the Colloid Vibration Current for a thin DL has been published in the book Dukhin, A. S. and Goetz, P. J. "Ultrasound for characterizing colloids. Particle sizing, Zeta Potential, Rheology", Elsevier, 2002. It is applies O'Brien's expression for introducing dynamic mobility as follows:

$$CVI = A(\omega)B(Z_T, Z_S)\varphi \frac{\rho_p - \rho_m}{\rho_m} \mu_d \nabla P \quad (4)$$

where $A(\omega)$ is an instrument constant found by calibration, $\omega$ is the ultrasound frequency, $B(Z_T, Z_S)$ is a function of the acoustic impedances of the transducer $Z_T$ and dispersion $Z_S$, $\rho_p$ and $\rho_m$ are the density of the particles and liquid media respectively, and P is the pressure of the ultrasound wave.

We also retain the same structure as O'Brien suggested for the dynamic electrophoretic mobility expression, presenting as separate multipliers both the inertial effects (function G) and the electrodynamic effects (function I+F). However, in contrast to the dilute case, functions G and F for concentrated systems depend on the particle concentration.

There is also an additional density dependent multiplier, $$\frac{(\rho_p - \rho_s)\rho_m}{(\rho_p - \rho_m)\rho_s},$$

which is equal to the ratio of the particle velocity relative to the liquid, and to the particle velocity relative to the center of mass of the dispersion. The convenience of the introduction of such a multiplier, which differs from unity only for concentrated suspensions, follows from the exact structure of Smoluchowski's asymptotic solution for $\mu_d$.

The corresponding equation, which in a convenient way reflects simultaneously limiting transformations both to Smoluchowski's asymptotic solution and to O'Brien's dilute case asymptotic solution, is given as follows:

$$\mu_d = \frac{2\varepsilon_0 \varepsilon_m S(\rho_p - \rho_s)\rho_m}{3\eta(\rho_p - \rho_m)\rho_s} G(s, \varphi)(1 + F(Du, \omega', \varphi)) \quad (5)$$

The generalization for the case of polydisperse systems is given by:

$$\mu_d = \frac{2\varepsilon_0 \varepsilon_m S(\rho_p - \rho_s)\rho_m}{3\eta(\rho_p - \rho_m)\rho_s} \sum_{i=1}^{N} G_i(s_i, \varphi)(1 + F_i(Du_i, \omega', \varphi)) \quad (6)$$

The new values of the functions G and F are given by the following equations:

$$G_i(s, \varphi) = \frac{9\varphi_i h(s_i)\rho_s}{4j\varphi(1-\varphi)s_i I(s_i)\left(\rho_p - \rho_m\left(\frac{3H_i}{2I_i}+1\right)\right)} \quad (7)$$
$$1 - \frac{\rho_p}{1-\varphi}\sum_{i=1}^{N}\frac{\varphi_i\left(\frac{3H_i}{2I_i}+1\right)}{\rho_p - \rho_m\left(\frac{3H_i}{2I_i}+1\right)}$$

$$F_i(Du_i, \omega', \varphi) = \frac{(1-2Du_i)(1-\varphi)+j\omega'\left(1-\frac{\varepsilon_p}{\varepsilon_m}\right)(1-\varphi)}{2(1+Du_i+\varphi(0.5-Du_i))+j\omega'\left(2+\frac{\varepsilon_p}{\varepsilon_m}+\varphi\left(1-\frac{\varepsilon_p}{\varepsilon_m}\right)\right)} \quad (8)$$

where $\epsilon_0$ is the dielectric permittivity of vacuum, $\eta$ is the dynamic viscosity, $\rho_s$ is the density of the system, $$s_i^2 = \frac{a_i^2 \omega \rho_m}{2\eta}, \quad \omega' = \frac{\omega}{\omega_{MW}}, \quad \omega_{MW} = \frac{K_m}{\varepsilon_0 \varepsilon_m},$$

$K_m$ is the conductivity of media, $\phi_i$ and $Du_i = \kappa^\sigma/K_m a_i$ is the volume fraction and Dukhin number for the ith fraction of the polydisperse colloid, respectively, and $\kappa^\rho$ is the surface conductivity. Special functions H and I are given in the book Dukhin, A. S. and Goetz, P. J. "Ultrasound for characterizing colloids. Particle sizing, Zeta Potential, Rheology", Elsevier, 2002.

These expressions are restricted to the case of a thin DL and are valid for a broad frequency range, including the Maxwell-Wagner relaxation range. They take into account both hydrodynamic and electrodynamic particle interaction, and are valid for polydisperse systems without making any superposition assumption.

FIG. 2 illustrates the dependence of the dynamic mobility on conductivity in the high conductivity range for non-conducting particles having a low dielectric permittivity. The dynamic mobility is practically independent of the real part of the conductivity for the range corresponding to typical aqueous systems, $K_m > 10^{-4}$. This observation forms the basis of the statements made by various authors quoted in the Background Art section of this patent.

However, as illustrated in FIG. 3, particles having a high dielectric permittivity, such as barium titanate, the dynamic mobility is very strong dependent on the conductivity of media. It is clear that for such particles information on conductivity and dielectric permittivity of particles is vital for adequate calculation of the $\zeta$-potential.

Electroacoustic Theory for Thick DL ($\kappa a < 0.1$).

As stated before, the DLs of particles fill the entire inter-particle space. The first version of the electroacoustic theory that takes into account this fact has been presented in the paper "The theory of electroacoustics in concentrated weakly-conducting suspensions", by Yu. B. Borkovskaya, V. N. Shilov and A. S. Dukhin, Abstracts of International Symposium on Electrokinetic Phenomena, Krakow, Poland, 2002, p. 35.

There is a bulk electric charge that is spread almost homogeneously throughout the inter-particle space in the case of the thick DL. In accordance with the theory of the equilibrium double layer, in this quasi-homogeneous case we may express the density of the screening charge as through an equilibrium electric potential that is identical to $\zeta$:

$$\sigma = \frac{RT}{F} \varepsilon_m \kappa^2 \sinh \frac{F\zeta}{RT} \quad (5)$$

where R is the gas constant and F is the constant.
The real part of the complex conductivity of the charged solution in the bulk of the dispersion equals:

$$K_m = \frac{D}{2} \varepsilon_m \kappa^2 \cosh \frac{F\zeta}{RT} \quad (6)$$

Where $\overline{D}$ is the average value of the diffusivities of the ions in the dispersion medium.

It is important to note that such a space-homogeneity of the value of the screening charge density and the conductivity of the inter-particle solution exists independently of any details of the geometry of the particle's surface. This remarkable feature leads to the following important conclusions concerning the electrokinetic phenomena:

i) The space distribution of convective electric current density $i_v$ caused by the movement of charged liquid is similar to the space distribution of the local liquid velocity, v, defined by:

$$i_v = \sigma v = v \frac{RT}{F} \varepsilon_m \kappa^2 \sinh \frac{F\zeta}{RT} \quad (7)$$

ii) The space distribution of conductive electric current density $i_e$, caused by the movement of ions in the dispersion medium between the particles surfaces under the action of applied electric field is similar to the space distribution of the electric current density for a concentrated electrolyte solution (with negligible contribution of the surface current)

$$i_e = K_m \Delta \Psi = \Delta \Psi \frac{D}{2} \varepsilon_m \kappa^2 \cosh \frac{F\zeta}{RT} \quad (8)$$

These peculiarities of systems with strongly overlapped DL lead to the following expression for CVI.

$$CVI = \frac{4RTa^2 K_m (\rho_p - \rho_s)}{9F\eta D\Omega \rho_s} \sinh \frac{F\zeta}{RT} \nabla P \quad (9)$$

where $\Omega(\phi)$ is hydrodynamic drag coefficient, equal to the ratio of the sedimentation velocity of the particles in suspension to that one of the isolated particle.

Following Eq.4, we can introduce the dynamic mobility for low conductivity systems:

$$\mu_d = \frac{4RTa^2 K_m (\rho_p - \rho_s)\rho_m}{9F\eta D\varphi \Omega(\rho_p - \rho_m)\rho_s} \sinh \frac{F\zeta}{RT} \quad (10)$$

It is seen that, contrary to the case of the thin DL, CVI and dynamic mobility become conductivity dependent. It turns out that it is impossible to eliminate this dependence by measuring potential (CVP) instead of current (CVI). The relationship between CVP and CVI indeed includes conductivity:

$$CVP = \frac{CVI}{K_s^*} \quad (11)$$

However, it is complex conductivity, whereas the expression for CVI includes only the real part of the complex conductivity.

The Complex conductivity reduces to the real conductivity if the Maxwell-Wagner frequency (see next section) is much higher than the frequency of the measurement. This condition is almost always valid in conducting aqueous systems, because the Maxwell-Wagner frequency is in this case very high, being proportional to the real conductivity.

In low conductivity systems, the Maxwell-Wagner frequency is much lower than the MHz range used for typical electroacoustic measurements. Consequently, the complex conductivity reduces to the imaginary part, which is independent of the real conductivity. The imaginary part depends on the dielectric permittivities of the particle and media:

$$K_s^*(\omega \gg \omega_{MW}) = j\omega\varepsilon_0\varepsilon_m \frac{E + 2\varphi}{E - \varphi} \quad (12)$$

where $$E = \frac{\varepsilon_p + 2\varepsilon_m}{\varepsilon_p - \varepsilon_m},$$

$\varepsilon_p$ is the dielectric permittivity of particles, and j is a unit complex number.

That leads us to the following expression for CVP:

$$CVP = \frac{4RTa^2 K_m (\rho_p - \rho_s)(\varphi - E)}{9F\eta D\Omega\rho_s j\omega\varepsilon_0\varepsilon_m (2\varphi + E)} \sinh\frac{F\zeta}{RT} \nabla P \quad (13)$$

We can conclude that in the case of thick and overlapped DLs ($\kappa a < 0.1$) the Electroacoustic signal depends on the conductivity in any mode, including ESA. All derivations for ESA are similar, except, perhaps, the density dependence, which is related to different inertial frame of reference.

FIG. 2 illustrates the dependence of the dynamic mobility on the real part of the conductivity of media.

Maxwell-Wagner Theory of the Complex Conductivity of Heterogeneous Systems.

The first electrodynamic cell model was applied for a pure electrodynamic problem by Maxwell and Wagner (see overview of the original works by Maxwell, J. C. "Electricity and Magnetism", Vol. 1, Clarendon Press, Oxford, 1892 and Wagner, K. W., Arch. Elektrotech., 2, 371, 1914 in the book by Dukhin, S. S. and Shilov V. N. "Dielectric phenomena and the double layer in dispersed systems and polyelectrolytes", John Wiley and Sons, NY, (1974)) for calculating the conductivity and dielectric permittivity of concentrated heterogeneous systems. This theory gives the following relationship between complex conductivity and dielectric permittivity:

$$\frac{\varepsilon_s^* - \varepsilon_m^*}{\varepsilon_s^* + 2\varepsilon_m^*} = \frac{\varepsilon_p^* - \varepsilon_m^*}{\varepsilon_p^* + 2\varepsilon_m^*} \varphi \quad (14)$$

$$\frac{K_s^* - K_m^*}{K_s^* + 2K_m^*} = \frac{K_p^* - K_m^*}{K_p^* + 2K_m^*} \varphi \quad (15)$$

where the index, s, corresponds to the colloid, m corresponds to the media, and p to the particle. The complex parameters are related to the real parameters as follows:

$$K_m^* = K_m - j\omega\varepsilon_o\varepsilon_m \quad (16)$$

$$\varepsilon_m^* = \varepsilon_m\left(1 + j\frac{K_m}{\omega\varepsilon_m\varepsilon_0}\right) \quad (17)$$

$$\varepsilon_p^* = \varepsilon_p + j\frac{2K_m Du}{\omega\varepsilon_0} \quad (18)$$

According to the Maxwell-Wagner theory, there is a dispersion region where the dielectric permittivity and the conductivity of the colloid are frequency dependent. Two simple interpretations exist for this Maxwell-Wagner frequency, $\omega_{MW}$. From DL theory it is the frequency of the DL relaxation relative to the external field disturbance. From general electrodynamics, it is the frequency at which the active and passive currents are equal. Thus $\omega_{MW}$ can be defined as two expressions:

$$\omega_{MW} = \kappa^2 D \frac{K_m}{\varepsilon_0\varepsilon_m} \quad (19)$$

If the measurement frequency is much lower than the Maxwell-Wagner frequency, the complex conductivity reduces to the real conductivity. In the opposite case of the frequency higher than Maxwell-Wagner frequency, the complex conductivity reduces to the imaginary part, which is dependent on dielectric permittivities.

FIG. 4 illustrates Maxwell-Wagner theory calculations for a barium titanate slurry.

FIG. 5 illustrates experimental verification of the Maxwell-Wagner theory. We performed this experimental test with aluminum hydroxide particles. The purpose of the test was to verify the volume fraction dependence predicted by the Maxwell-Wagner theory. We observe practically perfect agreement up to almost 50% vl. This test justifies the application of the Maxwell-Wagner theory for calculating unknown properties of the particles.

An Example of ζ-Potential Characterization in Low Conductivity Liquid: Iron Oxide Nanoparticles in Toluene-Bitumen Mixture.

FIG. 6 shows the CVI signal measured with a Model DT-1200 Zeta Potential probe for 15 nanometer iron oxide particles in a toluene-bitumen mixture. There is surfactant present for stabilizing the particles and inducing an electric surface charge.

The CVI signal in low conductivity media is typically much smaller than in aqueous systems. One factor that causes the lower signal is the dielectric permittivity of liquid, which is often 2040 times smaller than water. The lower CVI value in non-aqueous systems requires subtraction of the signal coming from the pure liquid, in order to extract that part of the measured signal contributed by the particles. This background signal for the pure liquid corresponds to the values with concentration equal to 0 on FIG. 6. The DT-1200 software subtracts the average of these several points from all subsequent measurements made for various concentrations of particles.

It can be seen that the CVI increases with increasing particle concentration, which is proof that the measured signal comes from the particles, and is not an artifact.

FIG. 7 shows ζ-potential values calculated from the measured CVI after background subtraction using Expression 9 with several different conductivities for the liquid. It is seen that variation of the conductivity causes significant variation of the ζ-potential. This is proof of the importance of independent conductivity measurement for adequate ζ-potential calculation in non-aqueous systems.

An Example Dispersion with Particles Having High Dielectric Permittivity: Barium Titanate in Water.

For dispersions containing particles having a high dielectric permittivity, it is clear that an adequate interpretation of the measured electroacoustic signal will require, first of all, an appropriate procedure for determining the dielectric permittivity of the particle material. We will use 20% wt barium titanate slurry to illustrate a novel method for accomplishing this task. According to the "Handbook of Chemistry and Physics", 70th Edition, 1989–1990, p. E-56, the dielectric permittivity of titanates, including Ba, varies from 15 to 12000, a wide range indeed.

If a dispersion contains particles with such high dielectric permittivity, then according to the Maxwell-Wagner theory we should expect a significant increase in the dielectric permittivity of the dispersion, as compared to that of the pure liquid. FIG. 3 illustrates this statement. The 20% wt barium titanate dispersion offers an easy way to verify this theoretical prediction. These barium titanate particles are heavy, having a density of 5 g/cm³, and hence even submicron sized particles settle very quickly. This rapid sedimentation offers a convenient way to verify this theoretical prediction. By not mixing, and allowing the particles to settle out, we can first measure the complex conductivity of the equilibrium supernate. Then, turning on an appropriate mixer, we can homogenize the sample, and then measure the complex conductivity of the complete dispersion. The imaginary part of the complex conductivity then yields information on the dielectric permittivity of both the supernate and the dispersion itself.

FIG. 8 shows the result of this test, performed using the conductivity probe of the Dispersion Technology DT-1200 at a frequency of 3 MHz. It is seen that the imaginary part of the complex conductivity of the dispersion exceeds that of the pure liquid supernatant, as expected. We can apply the Maxwell-Wagner theory (Eqns. 14–18) to calculate the dielectric permittivity of the particles from these data. Using this method, a dielectric permittivity of 850 was computed for this particular grade of barium titanate.

This computed dielectric constant for the particle then makes it possible to more accurately characterize the ζ-potential of the barium titanate dispersion, using thin DL electroacoustic theory described by Equations 4–8. FIG. 9 shows result of a pH titration of this slurry, starting at pH 8.7, using the Electroacoustic Zeta Potential probe of the DT-1200.

It is especially important that this method significantly improves the relationship between the phase of the experimental and theoretical CVI signal. FIG. 10 shows that there is a very large discrepancy between the experimental and theoretical phase if we assume a value of 3 for the dielectric permittivity of the particles. Increasing the dielectric permittivity of the particles to 850, based on the described procedure, significantly reduces this discrepancy. At the starting pH of 8.7, the experimental and theoretical phase are practically identical. This agreement gets somewhat worse with decreasing pH, which might be explained by some variation of the particle size. In any case, the agreement between theory and experiment is much improved over the whole pH range when the dielectric constant is set according to the value determined by the new procedure based on the inclusion of the conductivity measurement.

This improvement in the CVI phase data is important for the proper determination of the polarity of the ζ-potential. Phase values in the range 90°–270° correspond to negatively charged particles, while the remaining phase values correspond to positively charged particles. A large error in the phase interpretation related to the dielectric permittivity data might lead to a large phase error, and consequently a mistaken sign for the ζ-potential. The addition of the conductivity measurement to the characterization procedure improves both the absolute value of the ζ-potential and the reliability of its sign.

What is claimed is:

1. Method of characterizing the dielectric permittivity of particles dispersed in liquids, comprising a measurement of either the real or imaginary component of complex conductivity of an equilibrium supernatant (or filtrate), a measurement of the real or imaginary component of the complex conductivity of the homogeneous dispersion, and a calculation of the particle dielectric permittivity using the difference in either the real or imaginary components of the supernatant and homogeneous sample and the Maxwell-Wagner theory for the complex conductivity of heterogeneous systems.

2. Method of characterizing ζ-potential in dispersions and emulsions with unknown dielectric permittivity of particles with a double layer thickness that is less than particle radius comprising a measurement of Electroacoustic signal in either mode and a complex conductivity measurement and utilization of the standard electroacoustic theory for a thin double layer when said dielectric permittivity of particles would be determined from a complex conductivity measurement as suggested in claim 1.

3. Method of characterizing the ζ-potential of particles dispersed in liquids in which a double layer thickness is large compared to the particle radius, comprising a measurement of Electroacoustic signal in any one of the modes (CVI, CVP, or ESA), a measurement of complex conductivity real part, and utilization of the theory that interprets electroacoustic signal as oscillating motion of the charged particles in a homogeneous continuum of overlapped double layers with electric charge density that is independent of the space coordinate and said theory yields the following theoretical expression for calculating ζ-potential from the measured values of the Electroacoustic signal and real part of the complex conductivity:

$$CVP = \frac{4RTa^2 K_m (\rho_p - \rho_s)(\varphi - E)}{9F\eta D\Omega \rho_s j\omega \varepsilon_0 \varepsilon_m (2\varphi + E)} \sinh\frac{F\zeta}{RT} \nabla P$$

where $$E = \frac{\varepsilon_p + 2\varepsilon_m}{\varepsilon_p - \varepsilon_m};$$

R is the gas constant, T is absolute pressure, a is particle radius, $K_m$ is conductivity of liquid, $\rho_m$, $\rho_p$ and $\rho_s$ are densities of medium, particle and system, $\phi$ is volume fraction of solid, $\eta$ is dynamic viscosity, D is effective diffusion coefficient of ions, $\omega$ is frequency of ultrasound, $\Omega$ is drag coefficient, j is a complex unit, $\in_0$ and $\in_m$ are dielectric permittivities of vacuum and liquid, $\zeta$ is electrokinetic potential, $\nabla P$ is gradient of pressure is sound wave.

4. Method of characterizing the dielectric permittivity of non-conducting particles dispersed in liquids with known dielectric permittivity, comprising a measurement of the real and imaginary components of complex conductivity of homogeneous dispersion, which yields in this case sufficient information for calculating the particle dielectric permittivity using the Maxwell-Wagner theory for the complex conductivity of heterogeneous systems.

5. Method of characterizing the dielectric permittivity of particles dispersed in liquids, comprising a measurement of the magnitude and phase of the Electroacoustic signal in any one of the modes (CVI, CVP, or ESA), a measurement of complex conductivity real part, a computation of theoretical phase of the Electroacoustic signal, and adjustment of the dielectric permittivity of the particles till the theoretical phase of the Electroacoustic signal matches its measured value.

* * * * *